United States Patent
Glukhovsky et al.

(10) Patent No.: US 7,724,928 B2
(45) Date of Patent: May 25, 2010

(54) DEVICE, SYSTEM AND METHOD FOR MOTILITY MEASUREMENT AND ANALYSIS

(75) Inventors: Arkady Glukhovsky, Santa Clarita, CA (US); Mordechai Frisch, Moreshet (IL); Zvika Gilad, Haifa (IL); Daphna Levy, Carmiel (IL)

(73) Assignee: Given Imaging, Ltd., Yoqneam (IL)

( * ) Notice: Subject to any disclaimer, the term of this patent is extended or adjusted under 35 U.S.C. 154(b) by 1079 days.

(21) Appl. No.: 11/401,328

(22) Filed: Apr. 11, 2006

(65) Prior Publication Data

US 2006/0193505 A1 Aug. 31, 2006

Related U.S. Application Data

(63) Continuation-in-part of application No. 11/201,217, filed on Aug. 11, 2005, now Pat. No. 7,200,253, which is a continuation of application No. 10/175,148, filed on Jun. 20, 2002, now Pat. No. 6,944,316, which is a continuation of application No. PCT/IL02/00386, filed on May 19, 2002.

(60) Provisional application No. 60/673,803, filed on Apr. 22, 2005, provisional application No. 60/299,178, filed on Jun. 20, 2001.

(51) Int. Cl.
 *G06K 9/00* (2006.01)
 *A61B 1/04* (2006.01)
(52) U.S. Cl. .................. 382/128; 600/117; 600/160
(58) Field of Classification Search ............. 382/100, 382/107, 128, 276, 286; 348/65; 600/101, 600/103, 117, 118, 160
See application file for complete search history.

(56) References Cited

U.S. PATENT DOCUMENTS

| | | | | |
|---|---|---|---|---|
| 4,278,077 | A | 7/1981 | Mizumoto | 128/4 |
| 5,604,531 | A | 2/1997 | Iddan et al. | 348/76 |
| 5,993,378 | A | 11/1999 | Lemelson | 600/109 |
| 6,240,312 | B1 | 5/2001 | Alfano et al. | 600/476 |
| 6,428,469 | B1 | 8/2002 | Iddan et al. | 600/109 |
| 6,621,917 | B1 | 9/2003 | Vilser | 382/128 |
| 6,709,387 | B1 | 3/2004 | Glukhovsky et al. | 600/109 |
| 6,944,316 | B2 | 9/2005 | Glukhovsky et al. | 382/107 |
| 2002/0103417 | A1 | 8/2002 | Gazdzinski | 600/109 |
| 2004/0143182 | A1 | 7/2004 | Kucera et al. | 600/424 |

FOREIGN PATENT DOCUMENTS

| | | |
|---|---|---|
| DE | 344 0177 A1 | 6/1986 |
| JP | 4-144533 A | 5/1992 |
| WO | WO 99/30610 A1 * | 6/1999 |
| WO | WO 02/102223 A2 | 12/2002 |
| WO | WO 2004/004540 A2 | 1/2004 |

OTHER PUBLICATIONS

Rowell, Nancy D., Endoscopes Go Wireless, Biophotonics in Action, Photonics Spectra, Mar. 2001, pp. 60, 62.
PCT Search Report International Application No. PCT/IL02/00386; Mailing Date: May 1, 2003.

(Continued)

*Primary Examiner*—Andrew W Johns
(74) *Attorney, Agent, or Firm*—Pearl Cohen Zedek Latzer, LLP (57) ABSTRACT

A device, system and method for motility measurement and analysis. For example, a system includes a processor to determine contractile activity within a body lumen based on an analysis of data received from an autonomous in-vivo device.

16 Claims, 6 Drawing Sheets

OTHER PUBLICATIONS

E. Stathopulos; V. Schlageter; B. Meyrat; Y. Ribaupierre; P. Kucera: "Magnetic pill tracking: a novel non-invasive tool for investigation of human digestive motility" Neurogastroenterology and Motility, vol. 17, No. 1, Feb. 2005, pp. 148-154.

European Search Report; EP Application No. EP 06 11 2864; Completion date: Jun. 30, 2006.

US Office Action of U.S. Appl. No. 10/175,148 Dated Jun. 16, 2004.

US Office Action of U.S. Appl. No. 11/201,217 Dated Mar. 31, 2006.

Lewis, MD., Blair S., "The Utility of Capsule Endoscopy in Obscure Gastrointestinal Bleeding", Techniques in Gastrointestinal Endoscopy, vol. 5, No. 3, pp. 115-120, Jul. 2003.

\* cited by examiner

DEVICE, SYSTEM AND METHOD FOR MOTILITY MEASUREMENT AND ANALYSIS

PRIOR APPLICATIONS DATA

This application claims priority and benefit from U.S. Provisional Patent Application No. 60/673,803, titled "Device, System and Method for Motility Measurement and Analysis", filed on Apr. 22, 2005, which is hereby incorporated by reference in its entirety. Additionally, this application is a continuation-in-part of, and claims priority and benefit from, U.S. patent application Ser. No. 11/201,217, titled "Motility Analysis Within a Gastrointestinal Tract", filed on Aug. 11, 2005, issued on Apr. 3, 2007 as U.S. Pat. No. 7,200,253, which is hereby incorporated by reference in its entirety, and which is a continuation of U.S. patent application Ser. No. 10/175,148, titled "Motility Analysis Within a Gastrointestinal Tract", filed on Jun. 20, 2002, issued on Sep. 13, 2005 as U.S. Pat. No. 6,944,316, which is hereby incorporated by reference in its entirety, and which in turn is a National Phase application of International Patent Application Number PCT/IL02/00386, titled "Motility Analysis Within a Gastrointestinal Tract", filed on May 19, 2002, published on Dec. 27, 2002 as International Application Publication Number WO 02/102223, which is hereby incorporated by reference in its entirety, and which in turn claims priority and benefit from U.S. Provisional Patent Application No. 60/299,178, titled "Motility Analysis Within a Gastrointestinal Tract", filed on Jun. 20, 2001, which is hereby incorporated by reference in its entirety.

FIELD OF THE INVENTION

The present invention relates to the field of in-vivo sensing, and more particularly to the field of in-vivo imaging.

BACKGROUND OF THE INVENTION

Peristalsis within a gastro-intestinal (GI) tract may transport swallowed food and may aid in digestion and eventual evacuation. Peristalsis may result in pressure waves or contractions moving along the GI tract, thereby resulting in motility of a bolus or other object within the GI tract.

Certain pathological conditions may alter the normal motility within the GI tract. Low motility may be caused by, for example, an obstruction, a blockage, or other pathological condition. Motility disorders may be caused by, for example, nervous disorders, and may not necessarily be visible.

Some in-vivo sensing systems may include an in-vivo imaging device able to acquire and transmit images of, for example, the GI tract while the in-vivo imaging device passes through the GI lumen.

Other devices, systems and methods for in-vivo sensing of passages or cavities within a body, and for sensing and gathering information (e.g., image information, pH information, temperature information, electrical impedance information, pressure information, etc.), are known in the art.

SUMMARY OF THE INVENTION

Some embodiments of the invention may include, for example, devices, systems, and methods for measurement and analysis of motility and/or contractile activity of the GI tract.

Some embodiments may include, for example, a system having a processor to determine, measure, calculate and/or analyze motility and/or contractile activity within a body lumen based on analysis of data received from an in-vivo device.

Some embodiments may include, for example, determining said motility and/or contractile activity based on an analysis of localization data of said in-vivo device.

Some embodiments may include, for example, calculating a displacement of said in-vivo device within a pre-defined period of time and to determine said motility and/or contractile activity based on said displacement.

Some embodiments may include, for example, determining a high motility and/or contractile activity based on a high displacement of said in-vivo device within said pre-defined period of time.

Some embodiments may include, for example, determining a low motility and/or contractile activity based on a low displacement of said in-vivo device within said pre-refined period of time.

Some embodiments may include, for example, identifying a pattern in said localization data and to determine said motility and/or contractile activity based on said pattern.

Some embodiments may include, for example, calculating said localization data based on a radio frequency signal received from said in-vivo device.

Some embodiments may include, for example, calculating a velocity of said in-vivo device within a pre-defined period of time and to determine said motility and/or contractile activity based on said velocity.

Some embodiments may include, for example, determining said motility and/or contractile activity based on a change of said velocity within said pre-defined period of time.

Some embodiments may include, for example, identifying a pattern in a plurality of calculated velocities and to determine said motility and/or contractile activity based on said pattern.

Some embodiments may include, for example, determining motility, contractions, and/or contractile activity based on image analysis of images obtained by an in vivo imaging device. For exam, analysis of light intensity in a plurality of images acquired by the in-vivo device may be used to determine contractile activity of the GI tract.

Some embodiments may include, for example, determining motility, contractions, and/or contractile activity based on a brightness level of a plurality of images acquired by the in-vivo device.

In some embodiments, the in-vivo device may include, for example, an in-vivo imaging device, an in-vivo sensing device, an autonomous in-vivo device, and/or a swallowable capsule.

Embodiments of the invention may provide various other benefits or advantages.

BRIEF DESCRIPTION OF THE DRAWINGS

The subject matter regarded as the invention is particularly pointed out and distinctly claimed in the concluding portion of the specification. The invention, however, both as to organization and method of operation, together with containers, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Although a portion of the discussion may relate to in-vivo imaging devices, systems, and methods, the present invention is not limited in this regard, and embodiments of the present invention may be used in conjunction with various other in-vivo sensing devices, systems, and methods. For example, some embodiments of the invention may be used, for example, in conjunction with in-vivo sensing of pH, in-vivo sensing of temperature, in-vivo sensing of pressure, in-vivo sensing of electrical impedance, in-vivo detection of a substance or a material, in-vivo detection of a medical condition or a pathology, in-vivo acquisition or analysis of data, and/or various other in-vivo sensing devices, systems, and methods.

Some embodiments of the present invention are directed to a typically one time use or partially single use detection and/or analysis device. Some embodiments are directed to a typically swallowable in-vivo device that may passively or actively progress through a body lumen, e.g., the gastrointestinal (GI) tract, for example, pushed along by natural peristalsis. Some embodiments are directed to in-vivo sensing devices that may be passed through other body lumens, for example, through blood vessels, the reproductive tract, urinary tract, or the like. The in-vivo device may be, for example, a sensing device, an imaging device, a diagnostic device, a detection device, an analysis device, a therapeutic device, or a combination thereof. In some embodiments, the in-vivo device may include an image sensor or an imager. Other sensors may be included, for example, a pH sensor, a temperature sensor, a pressure sensor, sensors of other in-vivo parameters, sensors of various in-vivo substances or compounds, or the like Devices, systems and methods according to some embodiments of the present invention, including for example in-vivo sensing devices, receiving systems and/or display systems, may be similar to embodiments described in U.S. Pat. No. 5,604,531 to Iddan et al., entitled "In-vivo Video Camera System", and/or in U.S. Pat. No. 7,009,634, entitled "Device for In-Vivo Imaging", issued on Mar. 7, 2006, and/or in U.S. patent application Ser. No. 10/046,541, entitled "System and Method for Wide Field Imaging of Body Lumens", filed on Jan. 16, 2002, published on Aug. 15, 2002 as United States Patent Application Publication Number 2002/0109774, and/or in U.S. patent application Ser. No. 10/046,540, entitled "System and Method for Determining In-vivo Body Lumen Conditions", filed on Jan. 16, 2002, published on Aug. 15, 2002 as United States Patent Application Publication Number 2002/0111544, and/or in U.S. patent application Ser. No. 11/226,350, entitled "System and Method for Presentation of Data Streams", filed on Sep. 15, 2005, all of which are hereby incorporated by reference in their entirety. Devices and systems as described herein may have other configurations and/or sets of components. For example, an external receiver/recorder unit, a processor and a monitor, e.g., in a workstation, such as those described in the above publications, may be suitable for use with some embodiments of the present invention. For example, the present invention may be practiced using an endoscope, needle, stent, catheter, etc. Some in-vivo devices may be capsule shaped, or may have other shapes, for example, a peanut shape or tubular, spherical, conical, or other suitable shapes.

Some embodiments of the present invention may include, for example, a typically swallowable in-vivo device. In other embodiments, an in-vivo device need not be swallowable and/or autonomous, and may have other shapes or configurations. Some embodiments may be used in various body lumens, for example, the GI tract, blood vessels, the urinary tract, the reproductive tract, or the like. In some embodiments, the in-vivo device may optionally include a sensor, an imager, and/or other suitable components.

Embodiments of the in-vivo device are typically autonomous and are typically self-contained. For example, the in-vivo device may be or may include a capsule or other unit where all the components are substantially contained within a container, housing or shell, and where the in-vivo device does not require any wires or cables to, for example, receive power or transmit information. The in-vivo device may communicate with an external receiving and display system to provide display of data, control, or other functions. For example, power may be provided by an internal battery or an internal power source, or using a wired or wireless power-receiving system. Other embodiments may have other configurations and capabilities. For example, components may be distributed over multiple sites or units; and control information or other information may be received from an external source.

Although embodiments of the invention are not limited in this regard, the term "motility" as used herein may relate to or may include, for example, in-vivo movement or in-vivo displacement of an in-vivo device.

Although embodiments of the invention are not limited in this regard, the term "high motility" as used herein may relate to or may include, for example, a relatively large displacement and/or a relatively fast movement of an in-vivo device; whereas the term "low motility" as used herein may relate to or may include, for example, a relatively small displacement and/or a relatively slow movement of an in-vivo device.

Although embodiments of the invention are not limited in this regard, the term "contractile activity" as used herein may relate to or may include, for example, movement or contractions of a body lumen, e.g., the GI tract.

Figure 1:
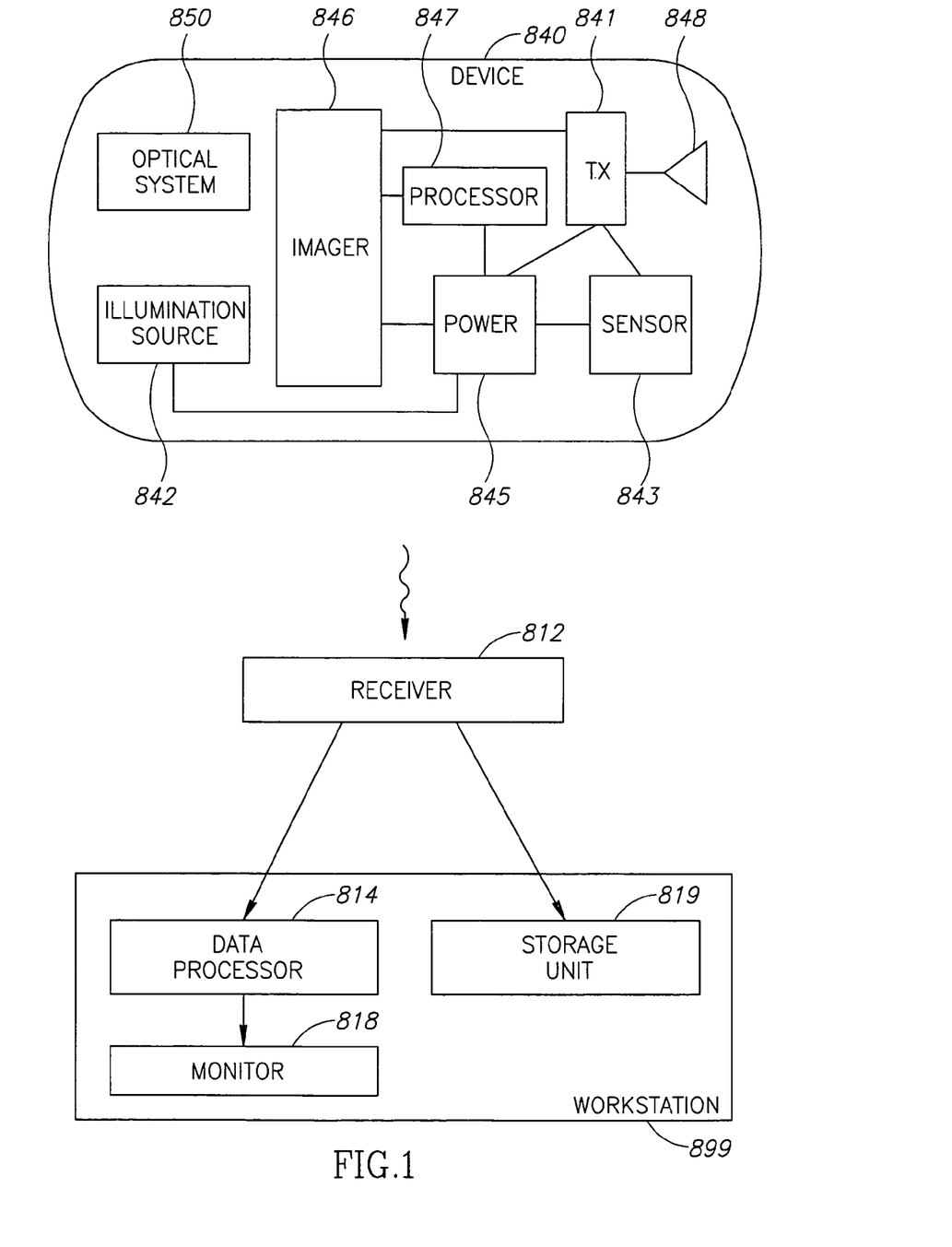
FIG. 1 is a schematic block diagram of an in-vivo sensing system in accordance with some embodiments of the invention.

FIG. 1 schematically illustrates an in-vivo sensing system in accordance with an embodiment of the present invention. In some embodiments, the system may include, for example, an in-vivo device 840 having an imager 846, an illumination source 842, a power source 845, and a transmitter 841. In some embodiments, device 840 may be implemented using a swallowable capsule, but other sorts of devices or suitable implementations may be used. Outside a patient's body may be, for example, an image receiver 812 (including or operatively connected to, for example, an antenna, an antenna belt, or an antenna array), a storage unit 819, a data processor 814, and a monitor 818. In one embodiment, for example, the storage unit 819, the data processor 814, and/or the monitor 818 may optionally be implemented as a workstation 899 which may include, for example, a multi-purpose or dedicated computer or computing platform.

Transmitter 841 may operate wirelessly, for example, by using radio waves; but in some embodiments, such as those where device 840 is or is included within an endoscope, transmitter 841 may transmit data via, for example, wire, optical fiber and/or other suitable methods.

Device 840 typically may be or may include an autonomous swallowable capsule, but device 840 may have other shapes and need not be swallowable or autonomous. Embodiments of device 840 are typically autonomous, and are typically self-contained. For example, device 840 may be a capsule or other unit where all the components are substantially contained within a container or shell, and where device 840 does not require any wires or cables to, for example, receive power or transmit information.

In some embodiments, device 840 may communicate with an external receiving and display system (e.g., through receiver 812) to provide display of data, control, or other functions. For example, power may be provided to device 840 using an internal battery, an internal power source, or a wireless system to receive power. Other embodiments may have other configurations and capabilities. For example, components may be distributed over multiple sites or units, and control information may be received from an external source.

In one embodiment, device 840 may include an in-vivo video camera, for example, imager 846, which may capture and transmit images of, for example, the GI tract while device 840 passes through the GI lumen. Other lumens and/or body cavities may be imaged and/or sensed by device 840. In some embodiments, imager 846 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In one embodiment, imager 846 in device 840 may be operationally connected to transmitter 841. Transmitter 841 may transmit images to, for example, image receiver 812, which may send the data to data processor 814 and/or to storage unit 819. Transmitter 841 may also include control capability, although control capability may be included in a separate component. Transmitter 841 may include any suitable transmitter able to transmit image data, other sensed data, and/or other data (e.g., control data) to a receiving device. For example, transmitter 841 may include an ultra low power Radio Frequency (RF) high bandwidth transmitter, possibly provided in Chip Scale Package (CSP). Transmitter 841 may transmit via antenna 848. Transmitter 841 and/or another unit in device 840, e.g., a controller or processor 847, may include control capability, for example, one or more control modules, processing module, circuitry and/or functionality for controlling device 840, for controlling the operational mode or settings of device 840, and/or for performing control operations or processing operations within device 840.

Power source 845 may include one or more batteries or power cells. For example, power source 845 may include silver oxide batteries, lithium batteries, other suitable electrochemical cells having a high energy density, or the like. Other suitable power sources may be used. For example, power source 845 may receive power or energy from an external power source (e.g., a power transmitter), which may be used to transmit power or energy to device 840.

In some embodiments, power source 845 may be internal to device 840, and/or may not require coupling to an external power source, e.g., to receive power. Power source 845 may provide power to one or more components of device 840, for example, continuously, substantially continuously, or in a non-discrete manner or timing, or in a periodic manner, an intermittent manner, or an otherwise non-continuous manner. In some embodiments, power source 845 may provide power to one or more components of device 840, for example, not necessarily upon-demand, or not necessarily upon a triggering event or an external activation or external excitement.

Optionally, in one embodiment, transmitter 841 may include a processing unit or processor or controller, for example, to process signals and/or data generated by imager 846. In another embodiment, the processing unit may be implemented using a separate component within device 840, e.g., controller or processor 847, or may be implemented as an integral part of imager 846, transmitter 841, or another component, or may not be needed. The optional processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In one embodiment, for example, the processing unit or controller may be embedded in or integrated with transmitter 841, and may be implemented, for example, using an ASIC.

In some embodiments, imager 846 may acquire in-vivo images, for example, continuously, substantially continuously, or in a non-discrete manner, for example, not necessarily upon-demand, or not necessarily upon a triggering event or an external activation or external excitement; or in a periodic manner, an intermittent manner, or an otherwise non-continuous manner.

In some embodiments, transmitter 841 may transmit image data continuously, or substantially continuously, for example, not necessarily upon-demand, or not necessarily upon a triggering event or an external activation or external excitement; or in a periodic manner, an intermittent manner, or an otherwise non-continuous manner.

In some embodiments, device 840 may include one or more illumination sources 842, for example one or more Light Emitting Diodes (LEDs), "white LEDs", Organic LEDs (OLEDs), or other suitable light sources. Illumination sources 842 may, for example, illuminate a body lumen or cavity being imaged and/or sensed. An optional optical system 850, including, for example, one or more optical elements, such as one or more lenses or composite lens assemblies, one or more suitable optical filters, or any other suitable optical elements, may optionally be included in device 840 and may aid in focusing reflected light onto imager 846 and/or performing other light processing operations.

Data processor 814 may analyze the data received via receiver 812 from device 840, and may be in communication with storage unit 819, e.g., transferring frame data to and from storage unit 819. Data processor 814 may also provide the analyzed data to monitor 818, where a user (e.g., a physician) may view or otherwise use the data, including, for example, image data, sensing data, location data, motility data, or other information. In one embodiment, data processor 814 may be configured for real time processing and/or for post processing to be performed and/or viewed at a later time. In the case that control capability (e.g., delay, timing, etc) is external to device 840, a suitable external device (such as, for example, data processor 814 or image receiver 812) may transmit one or more control signals to device 840.

Monitor 818 may include, for example, one or more screens, monitors, or suitable display units. Monitor 818, for example, may display one or more images or a stream of images captured and/or transmitted by device 840, e.g., images of the GI tract or of other imaged body lumen or cavity. Additionally or alternatively, monitor 818 may display, for example, control data, location or position data (e.g., data describing or indicating the location or the relative location of device 840), orientation data, motility information, and/or other suitable data. In one embodiment, for example, both an image and its position or location may be presented using monitor 818 and/or may be stored using storage unit 819. Other systems and methods of storing and/or displaying collected image data and/or other data may be used.

In some embodiments, in addition to or instead of revealing pathological or other conditions of the GI tract or other body lumens, the system may provide information about the location of these conditions. Suitable tracking devices and methods are described herein, as well as in embodiments of the above-mentioned U.S. Pat. No. 5,604,531 and/or U.S. patent application Ser. No. 10/150,018, titled "Array System and Method for Locating an In-Vivo Signal Source", filed on May 20, 2002, published on Nov. 21, 2002 as United States Patent Application Publication Number 2002/0173718, both of which assigned to the common assignee of the present invention and fully incorporated herein by reference. Other suitable location identification systems and methods may be used in accordance with embodiments of the present invention.

Typically, device 840 may transmit image information in discrete portions. Each portion may typically correspond to an image or a frame; other suitable transmission methods may be used. For example, in some embodiments, device 840 may capture and/or acquire an image once every half second, and may transmit the image data to receiver 812. Other constant and/or variable capture rates and/or transmission rates may be used.

Typically, the image data recorded and transmitted may include digital color image data; in alternate embodiments, other image formats (e.g., black and white image data) may be used. In some embodiments, each frame of image data may include 256 rows, each row may include 256 pixels, and each pixel may include data for color and brightness according to known methods. According to other embodiments, a 320 by 320 pixel imager may be used; other imagers having other suitable pixel sizes may be used. Pixel size may be, for example, between 5 to 6 microns; other suitable sizes may be used. According to some embodiments, pixels may be each fitted with a micro lens. For example, a Bayer color filter may be applied. Other suitable data formats may be used, and other suitable numbers or types of rows, columns, arrays, pixels, sub-pixels, boxes, super-pixels and/or colors may be used.

Optionally, device 840 may include one or more sensors 843, instead of or in addition to a sensor such as imager 846. Sensor 843 may, for example, sense, detect, determine and/or measure one or more values of properties or characteristics of the surrounding of device 840. For example, sensor 843 may include a pH sensor, a temperature sensor, an electrical conductivity sensor, a pressure sensor, or any other known suitable in-vivo sensor.

In some embodiments, device 840 may be capable of one way or two-way communication. For example, device 840 may be able to transmit data (e.g., sensed data, image data, localization data, or the like) using transmitter 841 to external receiver/recorder 812. Optionally, device 840 may be able to receive data (e.g., control data, instructions, commands, parameter values, modification of setting or parameters, activation instructions, deactivation instructions, or the like) from an external transmitter or transceiver. For example, in one embodiment, device 840 may optionally include a receiver able to receive signals (e.g., transmitter 841 may optionally be implemented as a transceiver or transmitter-receiver); and receiver/recorder 812 may optionally be implemented as a transceiver or transmitter-receiver able to transmit signals to device 840. Other suitable one-way or two-way communication mechanisms may be used.

In accordance with some embodiments of the invention, localization data may be determined using, for example, data collected by or transmitted by an in-vivo device (e.g., device 840 or another signal source) separate from location data itself. For example, localization data may be inherent in a signal sent by the in-vivo device 840, or may be in a beacon sent by the in-vivo device 840, while other and additional data such as sensing data (e.g., image data, pH data, etc.) may be sent separately from localization data. In one embodiment, sensing data may be considered non-localization data collected by the in-vivo device 840. In some embodiments, localization data may be inherent in a data signal which primarily contains sensed data In some embodiments, image data and other collected data may be stored for short-term or long term periods, transferred to other locations or devices, processed and/or analyzed. A health professional may use the images to diagnose pathological conditions of the GI tract or other body parts, and, the system may provide information about the location of these pathologies. In one embodiment, the data processor storage unit 819 may first collect data and then may transfer the data to the data processor 14, such that the image data is not viewed in real time. In an alternate embodiment, other configurations may allow real time viewing, and motility data and/or contractile activity data may be calculated and displayed substantially in real time.

The monitor 818 may present image data, preferably in the form of still and/or moving pictures, and in addition may present other information. For example, in one embodiment, the monitor may present the absolute time elapsed for the current image being shown, the relative or absolute motility of the device 840 over the course of the device 840 travel through the GI tract, contractile activity data or indicators, and/or the time corresponding to the current image or other data being displayed. Absolute time elapsed for the current image being shown may be, for example, the amount of time that elapsed between the moment the device 840 was first activated and the image receiver 812 started receiving transmissions from the device 840, and the moment that the current image being displayed was captured. Various methods may be used to display the motility of the device 840 and/or contractile activity, e.g. as discussed herein. In some embodiments, various types of information may be displayed in windows or other screen portions, and/or multiple monitors may be used to display image data, motility data, contractile activity data, localization data, and/or other data.

While, preferably, information gathering, storage and processing is performed by certain units, the system and method of the present invention may be practiced with alternate configurations. For example, components allowing motility and/or contractile activity analysis may be located inside device 840 (e.g., a swallowable capsule) or, alternatively, on a portable device (e.g., receiver 812) which may be worn on the patient. Furthermore, the components gathering image information need not be contained in a capsule, but may be contained in any other vehicle suitable for traversing a lumen in a human body, such as an endoscope, stent, catheter, needle, etc.

The in-vivo sensing system may collect a large volume of data, as the device 840 may take several hours to traverse the GI tract, and may record images at a rate of, for example, two images per second, resulting in the recordation of tens of thousands of images. The series of still images collected may later be presented as still images or as a moving image of the traverse of the GI tract. The image recordation rate (or frame capture rate) may be constant or variable; for example, the image recordation rate may be varied based on the motility of device 840.

While in the GI tract, the device 840 may undergo intermittent motion with relatively long residence time at some positions or locations. These periods of relatively long residence may be normal or may be due to pathologies, such as blockages, within the digestive tract. Embodiments of the present invention may, for example, aid health professionals in monitoring the device 840 motion and in diagnosing and locating, for example, areas of blockage or other pathologies. In addition, changes in motility may be indicative of a normal condition, for example, the passage of the device 840 from one section of the GI tract to another section, and thus embodiments of the present invention may use motility data to determine the position or location of the device 840 or other diagnostic device. In some embodiments, motility data may indicate on contractile activity and may allow generation of contractile activity data.

In one embodiment, substantially each image Pi in the data stream of images may be compared to its predecessor image Pi-1 (or to other previous image Pi-n), for example, to determine the motility of the device 840 and/or contractile activity during the time between the capture of the two images being compared. In accordance with embodiments of the invention, one or more methods of determining motility and/or contractile activity based on image comparison or image analysis may be used. In some embodiments, for example, images similarity or images difference may be determined and analyzed to obtain a measure or indication of motility and/or contractile activity. One embodiment, for example, may utilize an assumption that the more similar two compared images are, the slower the movement of the device 840 between the times the two images are captured. In accordance with one embodiment, if it is determined that taco compared images are substantially identical, it may be determined that the device 840 did not move between the times the two images were captured. In accordance with some embodiments, if two compared images differ greatly, it may be determined that the device 840 moved relatively quickly between the times of capture of the compared images.

In some embodiments, image comparison may be performed on a pixel-by pixel basis or and/or on a pixel cluster basis. In alternate embodiments, images may be compared without division into sections such as pixels or clusters. In one embodiment, a 256 by 256 pixel grid of each image may be divided into a 32 by 32 grid of pixel clusters, to form 1,032 clusters. In alternate embodiments, other methods of dividing an image may be used, and other numbers of pixels or dimensions may be used.

Based on, for example, the comparison of two or more images, data processor 814 may calculate contractile activity and/or the relative motility of the in-vivo imaging device 840 that captured the images for the time period between the capture of the two images. In one embodiment, the resulting motility value at a certain point may be a relative number on a scale, indicating the motility of the in-vivo imaging device 840 relative to other points in the device 840 traverse of the GI tract or other body part, and/or indicating on low or high contractile activity. In alternate embodiments, absolute motility may be calculated.

In some embodiments, contractile activity and/or motility calculation may be repeated for substantially all images or a set of images in the series of images, thereby generating a series of contractile activity and/or motility values. The resulting contractile activity and/or motility values may be presented to a user in various manners. In one embodiment, the monitor 818 may include a first window to display an image frame or a moving image, a second window to display the absolute time elapsed in the image series for the frame being displayed (or the current point in the moving image), and a third window to display a chart of contractile activity or the relative motility of the in-vivo imaging device 840 plotted against time and/or against distance traveled along a body lumen, e.g., the GI tract. An indication may be provided on the display on monitor 818 connecting certain contractile activity and/or motility values or patterns (e.g., regions having low motility or contractile activity, regions having high motility or contractile activity, or regions having certain motility or contractile activity patterns) to images or sections of the moving image. The user may indicate certain contractile activity or motility values, or a portion of the contractile activity or motility chart or plot by, for example, clicking with a mouse or using another input unit, and the system may thus display the corresponding still or moving image.

In some embodiments, additional windows may display other data. For example, the position of the in-vivo imaging device 840 as it traverses the GI tract may be graphed as a two-dimensional rendering of the three-dimensional path; such data may be combined with or linked to image data, contractile activity data and/or motility data. Areas of low motility or contractile activity, areas of high motility or contractile activity, or areas of altered or abnormal patterns of motility or contractile activity, may be indicated on such a path representation using, for example, color changes or labels.

In one embodiment, a spectral analysis of contractile activity or motility data may be performed, and the spectral analysis may be presented to the user or may be used for diagnostic or other purposes. For example, in a substantially normal human GI tract, peristaltic waves may be typically generated with some repetition. A spectral analysis of the peristaltic waves of different time periods or sections of the series of contractile activity or motility data, may be performed and presented to the user. Such a spectral analysis may present, for example, the frequency of repetition of peristaltic waves at different times or positions in a vehicle's travel through the GI tract. In alternate embodiments, other visual indications of contractile activity and/or motility may be provided.

In some embodiments, contractile activity data and/or motility data may be examined or analyzed to determine at least one parameter or measurement that may be presented as, for example, a specific pattern in a spectral analysis of the contractile activity or motility data, a representation of a pattern in a spectral analysis of the contractile activity or motility data, a specific repetition of peristaltic waves, or a representation of a repetition of peristaltic waves. The parameter, possibly represented by a pattern or specific patterns, may be compared to a reference, for example, a parameter value in a normal or healthy individual, or a specific pattern typical of a pathological condition in the GI tract. The comparison results may indicate, for example, a prevailing condition or conditions in the GI tract, thereby providing a diagnostic tool for identifying conditions in the GI tract. For example, a spectral analysis may be performed on the contractile activity or motility data of the in-vivo device 840. The spectral analysis may be represented, for example, as a graph of movement waves over time; other ways of representing a spectral analysis may be used. A pattern matching module (for example, implemented using processor 814 operating according to a software application) may seek to match the recorded spectral analysis with spectral analyses corresponding to various conditions, and a match or near-match may be determined and reported to a user.

In some embodiments, one or more methods may be used to analyze the image data to generate motility data and/or contractile activity data. For example, contractile activity and/or motility analysis may be based on a calculation of the difference in a given property between corresponding pixels of two or more, consecutive or non-consecutive, frames or images or image portions; a calculation of the cross-correlation function between two or more, consecutive or non-consecutive, frames or images or image portions; a calculation of the changes of local statistical distributions in two or more, consecutive or non-consecutive, frames or images or image portions; or a calculation of the changes between corresponding local statistical distributions in two or more, consecutive or non-consecutive, frames or images or image portions. Local statistical distributions may include, for example, the mean, the variance, or the standard deviation of one or more pixel clusters.

In some embodiments, image analysis may be used to determine the location of the device 40 in-vivo (for example, by identifying image parameters that are typical to a specific region in the GI tract or other body lumen). In some embodiments, the location or position information, as well as other factors (e.g., the time that has elapsed during the translocation of the device 840, or the velocity of the device 840 along its path) may be used to calculate motility and/or contractile activity. Similarly, the location of the device 840 may be determined by other methods, and the location information may be used to calculate motility and/or contractile activity.

Some embodiments may use one or more methods of measuring motility and/or contractile activity which may not be based on image analysis. For example, the device 840 may include an accelerometer, which may determine the instantaneous acceleration of device 840 as it moves through the GI tract. An integrator may convert the acceleration data to velocity data, and the velocity data may be used by the data processor 814 to determine motility and/or contractile activity.

In some embodiments, a pressure sensor or shear gauge may be attached to or included in the device 840, to allow detection of peristaltic-induced pressure or movement exerted by the walls of the intestine. According to some embodiments the relationship between pressure and velocity may be determined empirically, and then utilized to determine the velocity or relative velocity of the device 840.

In some embodiments, a sensor in the device 840 may detect movement relative to an artificially induced magnetic field, which may be generated in the area of the patient's GI tract. The magnetic field may induce a current in a coil in the sensor, whose magnitude may be a function of the velocity of the coil through the field. Data on the induced current may be analyzed and converted to motility and/or contractile activity information.

In some embodiments, external sensors may be used, for example, a Doppler ultrasound unit, which continuously tracks the device 840. Additionally or alternatively, the receiver 812, which, according to one embodiment is adapted to receive RF signals from transmitter 841 of device 840, may be used to monitor the intensity of the transmitted signal, whereas signals of unchanging intensities indicate that transmitter 841 (and hence the device 840) is unmoving, and signals of different intensities indicate that the transmitter 841 (and hence the device 840) is moving. One or more of these methods, and/or other suitable methods, may be combined to provide a determination of the motility of device 840 and/or contractile activity of a body lumen.

In some embodiments, contractile activity and/or motility may be determined based on localization of the in-vivo device 840, e.g., based on a determined displacement of the in-vivo device 840 over time or over a pre-defined period of time or time interval.

Figure 2:
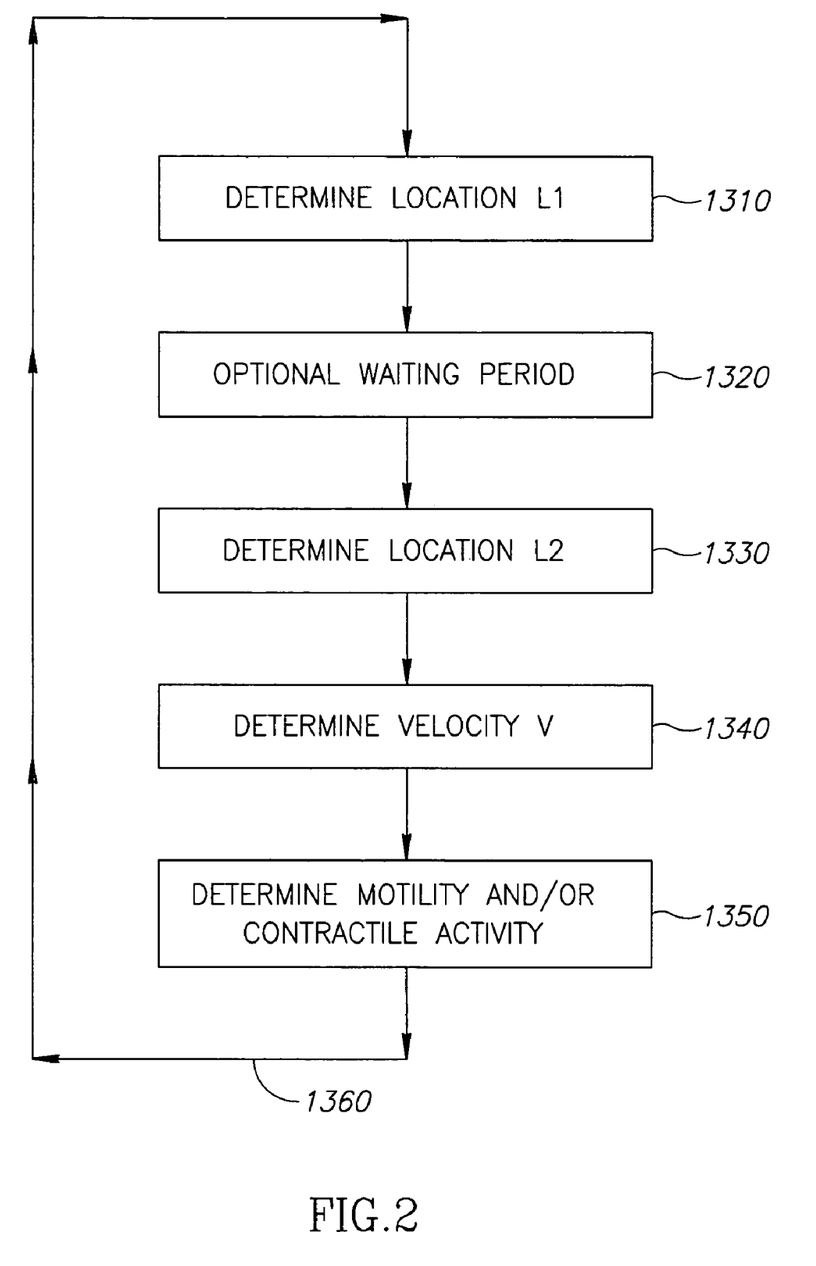
FIG. 2 is a flow chart of a method of determining motility and/or contractile activity based on localization data, in accordance with some embodiments of the invention.

Reference is made to FIG. 2, which is a flow-chart of a method of determining contractile activity and/or motility based on localization data, in accordance with some embodiments of the invention.

As indicated at box 1310, the method may include, for example, determining a location L1 of an in-vivo device at a first time point T1. For example, based on signal strength or other received signal analysis, receiver 812 and/or data processor 814 may determine the location L1 of the in-vivo device 840 at a first time point T1.

As indicated at box 1320, optionally, a waiting period or delay period may elapse between the operations of box 1310 and the operations of box 1310. For example, in one embodiment, a time interval of approximately one second, five seconds, ten seconds, or the like, may elapse. In alternate embodiments, other suitable time intervals may elapse, or substantially no delay period may elapse.

As indicated at box 1330, the method may include, for example, determining a location L2 of the in-vivo device at a second time point T2. For example, based on signal strength or other received signal analysis, receiver 812 and/or data processor 814 may determine the location L2 of the in-vivo device 840 at a second time point T2.

As indicated at box 1340, the method may include, for example, determining the velocity V of the in-vivo device between the first and second time points. For example, in one embodiment, a difference or absolute difference between L1 and L2 may be calculated, and may be divided by the difference or absolute difference between T1 and T2. In some embodiments, the following equation may be used:

$$V=|(L2-L1)/(T2-T1)| \qquad \text{Equation 1}$$

Other suitable equations or calculations may be used.

As indicated by arrow 1350, motility data and/or contractile activity data may be determined based on analysis (e.g., substantially real-time analysis) of the velocity data and/or the localization data. In one embodiment, for example, a calculated velocity V may be compared to a threshold value of velocity. If the calculated velocity V is greater than the threshold value, then it may be determined that the in-vivo device has relatively high motility in the time period between T1 and T2, and/or that the patient has a relatively high contractile activity (e.g., number of contractions per minute) in the time period between T1 and T2. If the calculated velocity V is smaller than the threshold value, it may be determined that the in-vivo device has relatively low motility or substantially no motility in the time period between T1 and T2, and/or that the patient has a relatively low or substantially no contractile activity (e.g., number of contractions per minute) in the time period between T1 and T2. In one embodiment, the threshold value may be pre-defined or pre-calculated, e.g., based on localization data pre-obtained from healthy patients and/or non-healthy patients; in another embodiment, the threshold value may be calculated in substantially real-time, e.g., based on an analysis or averaging of velocities of the in-vivo device.

As indicated by arrow 1360, the operations of boxes 1310-1350 may be repeated, e.g., periodically or substantially continuously.

In some embodiments, an analysis of determined velocity values or localization data may be performed to identify patterns or data indicating low or high motility, or indicating low or high contractile activity. For example, localization data and/or velocity values may be charted using a graph, and patterns on the graph may be identified to indicate low or high motility, or to indicate low or high contractile activity.

Figure 3:
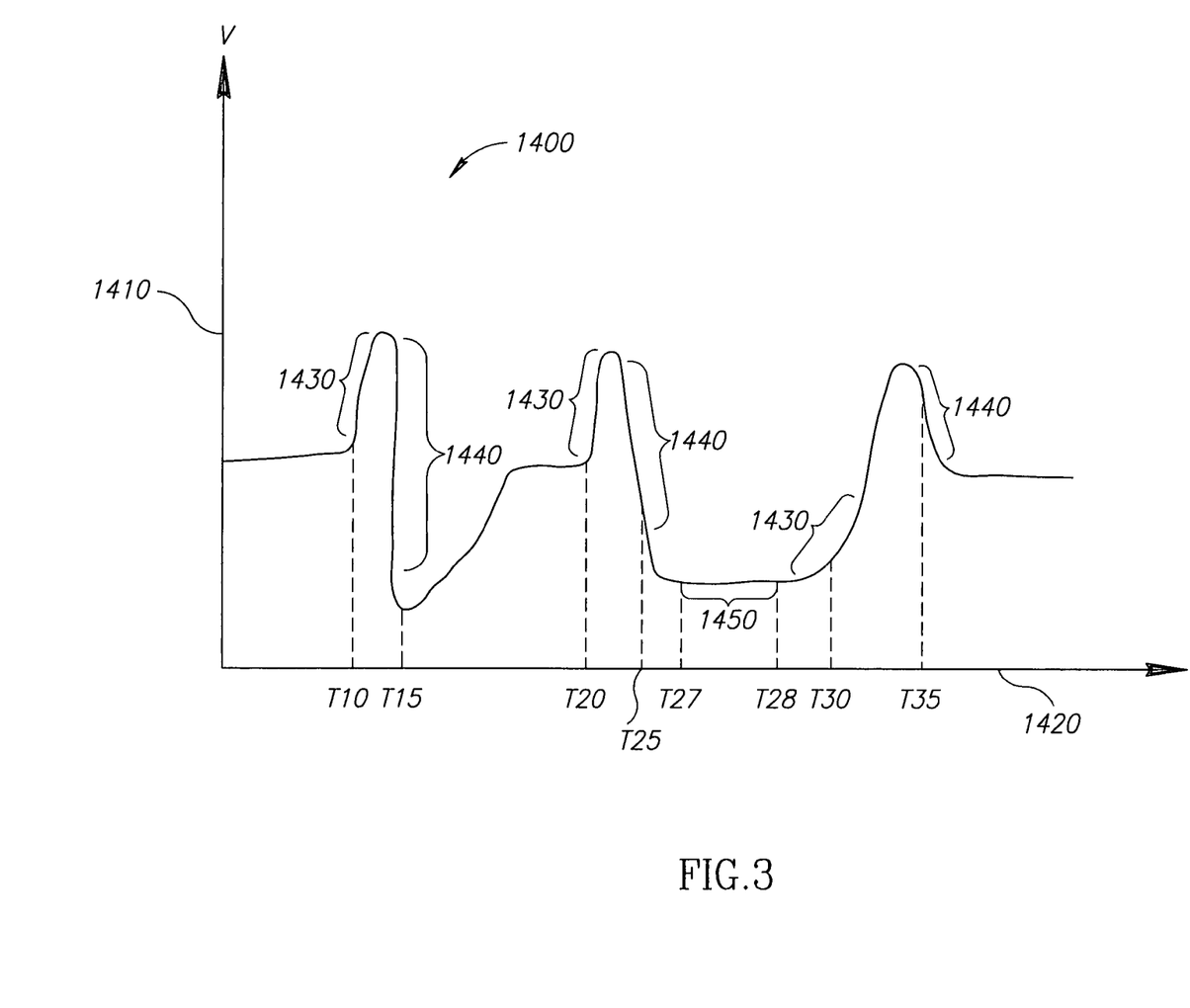
FIG. 3 is a schematic illustration of a graph of determined velocity values of an in-vivo device in accordance with some embodiments of the invention.

In some embodiments, a graph of determined velocity values may be prepared and analyzed, for example, to allow determination of motility or contractile activity. Reference is made to FIG. 3, which schematically illustrates a graph 1400 of determined velocity values of an in-vivo device in accordance with some embodiments of the invention. In graph 1400, a vertical axis 1410 may represent velocity (V) values, and a horizontal axis 1420 may represent time (T) values. In other embodiments, vertical axis 1410 may represent velocity (V) values, and horizontal axis 1420 may represent distance and/or location along a body lumen, e.g., a GI tract.

In some embodiments, a relatively sharp increase in velocity may be identified, for example, as indicated by patterns 1430 or other suitable patterns or data. The identified patterns may allow a determination that at corresponding time points (e.g., time points T10, T20 and T30) high motility took place, a high contractile activity took place, or that one or more contractions took place.

In some embodiments, a relatively sharp decrease in velocity may be identified, for example, as indicated by patterns 1440 or other suitable patterns or data The identified patterns may allow a determination that at corresponding time points (e.g., time points T15, T25 and T35) low motility or low contractile activity took place.

In some embodiments, a relatively non-changing velocity may be identified, for example, as indicated by pattern 1450 or other suitable patterns or data. The identified pattern may allow a determination that at one or more corresponding time points (e.g., time points T27 and T28) low motility took place, low contractile activity took place, or substantially no contractions took place.

Other suitable determinations with regard to motility and/or contractile activity may be performed based on analysis of velocity data and/or localization data.

In some embodiments, contractile activity may be determined based on one or more indicators. In one embodiment, for example, a relatively high contractile activity may be determined based on identification of a relatively large displacement of the in-vivo device (e.g., determined using localization data) over a relatively short pre-defined period of time; and a relatively low contractile activity may be determined based on identification of a relatively low displacement of the in-vivo device (e.g., determined using localization data) over a relatively long pre-defined period of time. In another embodiment, for example, relatively high or relatively low contractile activity may be determined based on analysis of motility data, velocity data, displacement data and/or localization data of the in-vivo device.

In some embodiments, multiple images acquired by the in-vivo device may be compared to allow determinations with regard to contractile activity. In one embodiment, for example, image comparison (or cluster comparison) may indicate that a subsequent image differs greatly from a previous image, thereby allowing a possible determination that a relatively high contractile activity took place between the times in which the compared images were captured. In another embodiment, for example, image comparison (or cluster comparison) may indicate that a subsequent image differs little from a previous image, thereby allowing a possible determination that a relatively low contractile activity or substantially no contractile activity took place between the times in which the compared images were captured.

In some embodiments, a pathology, a possible medical diagnosis, a medical condition, and/or a medical diagnosis may be determined or suggested, for example, based on motility data and/or contractual activity data. In one embodiment, for example, relatively low motility and/or relatively low contractile activity may be used to suggest or determine that a patient may have a dysfunctional or malfunctioning bowel movement, a dysfunctional or malfunctioning bowel segment, or the like.

In some embodiments, one or more data items, data patterns, determinations or other analysis results, may be used to identify or determine a contraction, or to identify or determine contractile activity. In one embodiment, for example, a relatively sharp change or decrease of illumination (e.g., overall illumination) in one or more image may be used to determine a contraction or contractile activity. In another embodiment, for example, a relatively sharp change or increase in velocity, position and/or location of the in-vivo device may be used to determine a contraction or contractile activity.

In yet another embodiment, for example, a motion or displacement of the in-vivo device "backwards" or upstream, e.g., not in accordance with the general direction of progress of the in-vivo device, may be used to determine a contraction or contractile activity; this may result in, for example, of a contraction engaging only a part of the in-vivo device (e.g., the frontal part or tip of the in-vivo device), or of a contraction downstream causing a fluid above the contraction area to be pushed upstream.

In one embodiment, motility data and/or contractile activity data may be compared with, or analyzed in relation to, corresponding data describing motility and/or contractile activity of typically healthy persons, typically unhealthy persons, persons having one or more diseases or medical conditions, or the like. Such comparison or analysis may allow, for example, suggesting or determining that the motility data and/or contractile activity data collected from a patient indicate (or more-likely indicate) that the patient is healthy, unhealthy, has one or more diseases or medical conditions, or the like.

In some embodiments, motility data, localization data, position data, velocity data, acceleration data, illumination data, image comparison results, or other data, may be analyzed or determined over time, e.g., periodically, substantially continuously, over a pre-defined period of time, in accordance with pre-defined time intervals or time slots, or the like.

In some embodiments, motility, a contraction and/or contractile activity may be determined based on illumination data, e.g., changes if an intensity of illumination in one or more images acquired by the in-vivo device. In some embodiments, for example, a contraction or contractile activity may alter the distance between the in-vivo device and the lumen which may surround it, thereby modifying the amount or intensity of light reflected from the lumen to the imager of the in-vivo device. In some embodiments, light modulation may be correlated with motility, contractile activity, or contractions. In some embodiments, the in-vivo imaging device may acquire images of a relatively small cavity located between the in-vivo imaging device and the body lumen; accordingly, light modulation in that cavity, which may be related to contractions or contractile activity, may be used for determining contractions, contractile activity, or motility.

Figure 4:
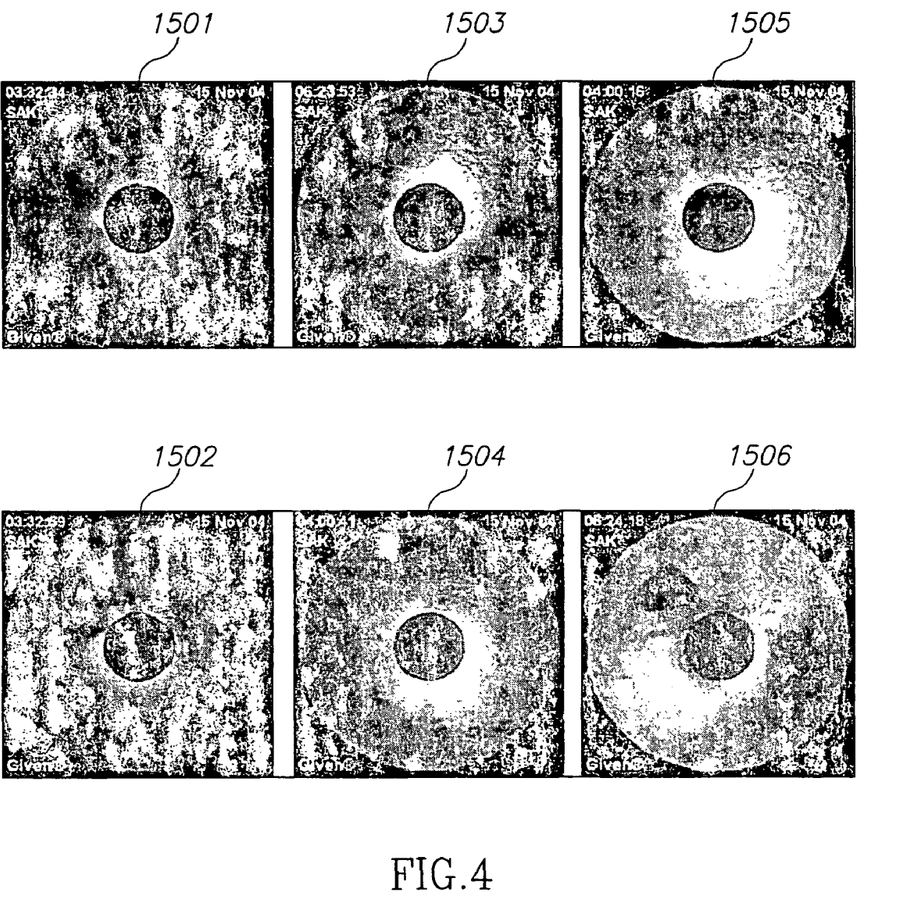
FIG. 4 is an illustration of six exemplary frames acquired by an in-vivo imaging device and which may be used to determine motility, contractions and/or contractile activity in accordance with some embodiments of the invention.

According to one embodiment an autonomous capsule shaped imaging device is used for obtaining images of the GI tract lumen, which may have a circular field of view that is substantially at a right angle to the long axis of the capsule shaped device. In some embodiments, an area of the imaging device may be concave, tapered, narrowed or 'pinched' so that the device may have a shape resembling a peanut. Such concave area may for example include a transparent ring, segment or viewing window through which light may enter and be reflected off of a reflective surface (e.g., a portion of the GI tract wall) onto an image sensor. Device may include one or a plurality of illuminators that may illuminate an endo-luminal wall or area from for example one or several directions. Light rays reflecting off of an endo-luminal wall may strike reflective surface in the device and be reflected onto the image sensor. In some embodiments the reflective surface may be in a parabolic shape, such that for example light rays striking reflective surface from various directions will be reflected towards the image sensor. Typically, in a tube-like lumen, a contraction may cause a capsule shaped device to become aligned with the lumen axis. Thus, an imaging capsule moving along a GI tract lumen, e.g., the small intestine, and having a substantially perpendicular field of view may be, according to one embodiment, sensitive to contraction of the GI tract lumen since these contractions may cause the lumen wall to collapse or constrict upon the longitudinal walls of the imaging capsule, through which an image is obtained, blocking and/or altering the field of view and/or illumination of the field of view. Images obtained from such an imaging capsule shaped device may look like the exemplary frames shown in FIG. 4. For example, the in-vivo imaging device may include an imager able to acquire panoramic (e.g., ring-shaped) images, as shown in FIG. 4 and as detailed herein. Thus, in one embodiment, for example, one or more in-vivo images which are dark or relatively darker, may indicate that a contraction took place at the time the image or images were acquired; in another embodiment, one or more images which are bright or relatively brighter, may indicate that a contraction did not take place at the time the image or images were acquired. For example, a contraction of the body lumen or a portion thereof may cause the lumen wall to constrict upon the external portion of the in-vivo device through which panoramic in-vivo images are acquired, thereby blocking the panoramic field of view of the in-vivo imager and resulting in a dark panoramic (e.g., ring-shaped) in-vivo image; accordingly, a dark or relatively dark panoramic image may correspond to a contraction of the body lumen around or near the in-vivo imaging device, e.g., the in-vivo imaging device able to acquire panoramic images.

In an alternate embodiment, for example, a substantially reversed determination may be used, such that, for example, brighter images may indicate a contraction whereas darker images may indicate no or less contractile activity. According to one embodiment, a forward or backward looking capsule shaped imaging device may be used in which a body lumen tissue is illuminated and imaged through a dome shaped window. During a contraction the capsule shaped device may typically be aligned with the longitudinal axis of the tube-like lumen. According to one embodiment, the lumen tissue that is, in a relaxed state of the lumen, close to being parallel to the capsule walls, becomes in a constricted phase, closer to being perpendicular to the capsule walls, typically being brought closer to the capsule dome. Due to the dome covering the illumination source and imager, the tissue not brought close enough to obstruct the field of view, such that light reflected off the now closer tissue wall may be brighter in the image obtained of that tissue. Thus, according to one embodiment, during a contraction an image of the tissue may typically be brighter than an image obtained during a relaxed phase of the lumen. For example, an in-vivo device able to acquire images utilizing a frontal field of view, may acquire a first image having a first illumination level (e.g., a relatively bright image) when the body lumen contracts and when the imager's field of view has a first size or depth due to the contraction; whereas the in-vivo device may be able to acquire a second image having a second, different, illumination level (e.g., a relatively dark image) when the body lumen does not contract and when the imager's field of view has a second, different, size or depth due to the absence of contractions. For example, the contraction or absence thereof may modify the content of the field of view of the in-vivo imager, e.g., such that a body lumen or a portion thereof may be closer or farther in relation to the in-vivo imager, thereby modifying the level of illumination (e.g., brightness or darkness) of the acquired in-vivo images, and allowing to determine occurrence or absence of contractions based on the level of illumination of acquired images.

In another embodiment, for example, a one or more patterns of dark images and bright images may be identified, and it may be determined that substantially each such pattern (e.g., having a series of dark images and bright images, or vice versa) indicates a contraction. Other suitable analysis methods and determinations may be used.

Reference is made to FIG. 4, which illustrates six exemplary frames 1501-1506 acquired by an in-vivo imaging device and which may be used to determine motility, contractions and/or contractile activity in accordance with some embodiments of the invention. Although six exemplary frames 1501-1506 are shown, other frames or images may be acquired, used or analyzed in accordance with embodiments of the invention.

Frame 1501 shows an exemplary image acquired by the in-vivo imaging device when a substantially full contraction takes place in proximity to the in-vivo imaging device; and frame 1502 shows an exemplary image acquired by the in-vivo imaging device when a contraction takes place in proximity to the in-vivo imaging device. As shown in frames 1501 and 1502, the contraction resulted in relatively darker images.

Frames 1503, 1504 and 1505 show exemplary images acquired by the in-vivo imaging device in a "regression" period, e.g., when the body lumen returns from its state in a contraction to its "idle" state having substantially no contractile activity. As shown in frames 1503-1505, images acquired by the in-vivo device during this period of time may be relatively brighter, or relatively less dark, then the images of frames 1501-1502.

Frame 1506 shows an exemplary image acquired by the in-vivo imaging device when the body lumen is in its "idle" state having substantially no contractile activity. As shown in frame 1506, images acquired by the in-vivo device during this period of time may be significantly brighter, or significantly less dark, than the images of frames 1501-1502; and may be relatively brighter, or relatively less dark, than the images of frames 1503-1505.

It is noted that the images of frames 1501-1506 are presented for exemplary purposes only; embodiments of the invention may produce and/or use other images having various degrees of brightness, darkness, relative brightness, relative darkness, light intensity, illumination intensity, or the like, and may use such images to produce other determinations with regard to motility, contractions, or contractile activity.

In some embodiments, the in-vivo images of frames 1501-1506 may be acquired using an in-vivo imaging device having a panoramic field of view, or using an in-vivo imager able to acquire panoramic (e.g., ring-shaped) in-vivo images.

Figure 5:
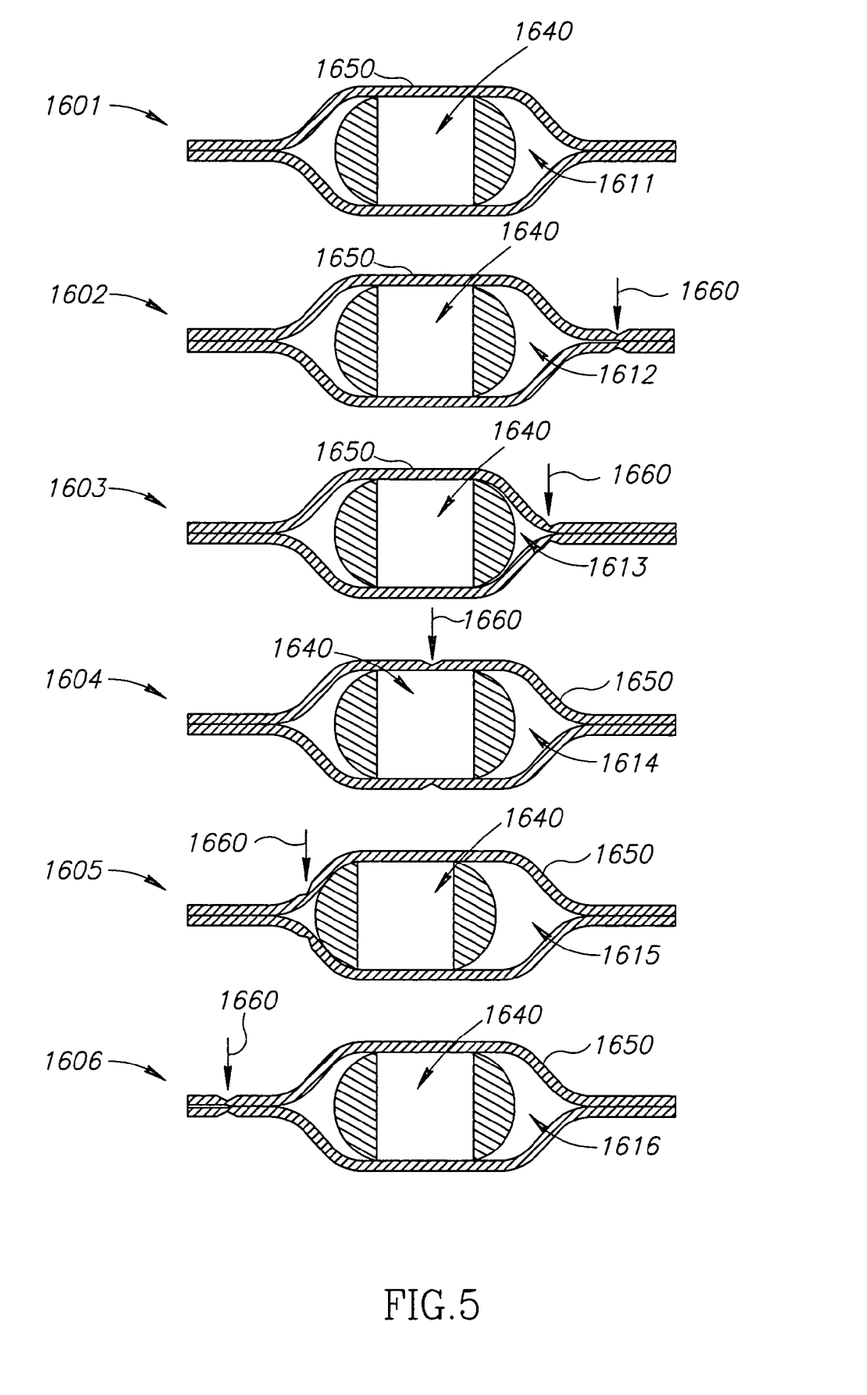
FIG. 5 is a schematic illustration of six exemplary stages of an in-vivo device passing through a body lumen in accordance with some embodiments of the invention.

Reference is made to FIG. 5, which schematically illustrates six exemplary stages 1601-1606 of an in-vivo device 1640 passing through a body lumen 1650 in accordance with some embodiments of the invention. Stage 1601 shows no contraction, whereas stages 1602-1606 show (as indicated by an arrow 1660) a contraction propagating through the body lumen 1650. Although six exemplary stages are 1601-1606 are shown, other numbers or types of stages may be used in accordance with embodiments of the invention.

As shown in FIG. 5, in each of stages 1601-1606, a cavity (referenced with numerals 1611-1616, respectively) may exist between the in-vivo device 1640 and the body lumen 1650. The size or volume of the cavity 1611-1616 may change, for example, as the contraction propagates through the body lumen 1650. In some embodiments, the light reflected by the body lumen 1650 onto the imager of in-vivo device 1640 may change (e.g., in relation, or in reverse relation) to the size or volume of the cavity 1611-1616.

In some embodiments, a contraction propagating through the body lumen 1650, may change or modulate the size or volume of the cavity 1611-1616, thereby changing or modulating the intensity of light reflected onto the imager of in-vivo device 1640. In some embodiments, the light modulation may be periodic, such that the average intensity of the images acquired by the in-vivo imaging device 1640 (e.g., without or prior to applying gain correction techniques) may be modulated by contractions of body lumen 1650.

Figure 6:
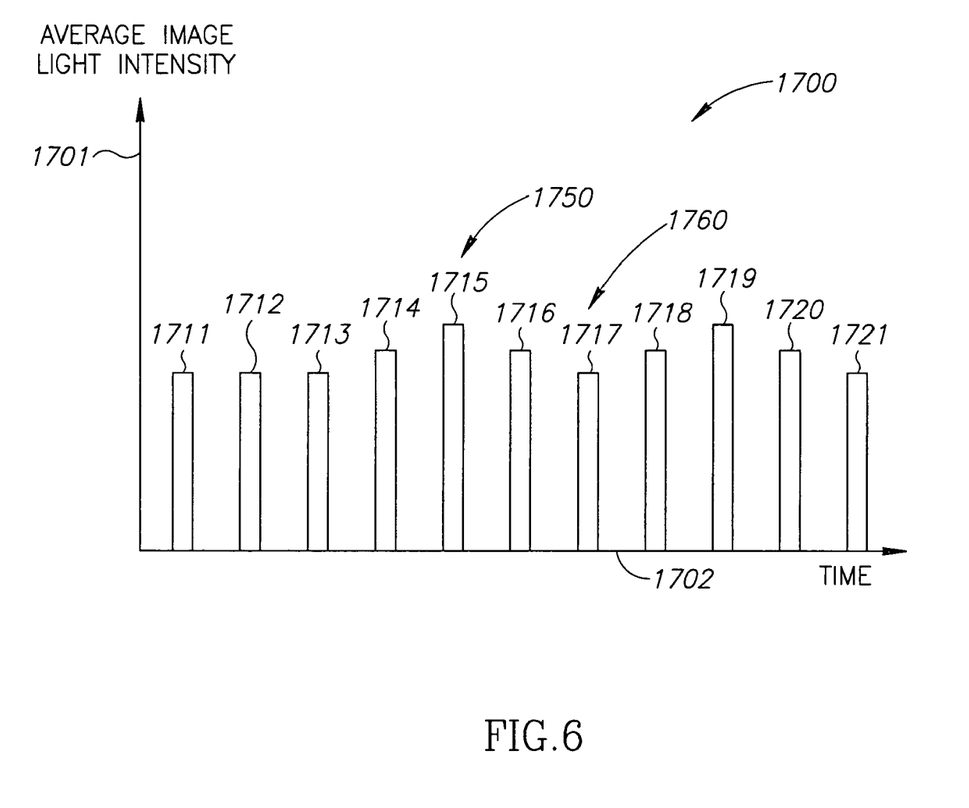
FIG. 6 is a schematic illustration of a graph of average image light intensity of images acquired by an in-vivo imaging device in accordance with some embodiments of the invention.

Reference is made to FIG. 6, which schematically illustrates a graph 1700 of average image light intensity of images acquired by an in-vivo imaging device in accordance with some embodiments of the invention. A vertical axis 1701 may indicate an average image light intensity; a horizontal axis 1702 may indicate time (or, in some embodiments, images, or sets of images). Bars 1711-1721 may indicate average light intensity of images acquired by the in-vivo device.

As shown in graph 1700, the average image light intensity may increase and decrease over time, and may be used, for example, as a modulation signal related to contractile activity or contractions. In one embodiment, the modulation signal strength may be relatively low, and may have a relatively low Signal to Noise Ratio (SNR); yet the modulation signal may be periodic and may have a one or more measurable parameters. For example, in some embodiments, the amplitude or frequency of the modulation signal may be determined, and may optionally be determined to correlate to the amplitude or frequency of contractile activity. In some embodiments, the amplitude and/or frequency of the modulation signal may be compared to, for example, amplitude or frequency of a modulation signal of a healthy person, a non-healthy person, a person having one or more diseases or medical conditions, or the like. In one embodiment, the modulation signal may be further analyzed or processed, for example, using one or more filters, to generate determinations with regard to motility, contractions, or contractile activity.

In one embodiment, a "peak" 1750 in the modulation signal, or a pattern of increased average image light intensity, may indicate a contraction. In an alternate embodiment, a "dip" 1760 in the modulation signal, or a pattern of decreased average image light intensity, may indicate a contraction. In some embodiments, peak 1750 and dip 1760 may be used to determine one contractile activity in the time period which corresponds to that peak 1750 and dip 1760. In some embodiments, other patterns or portions in graph 1700 may indicate contractile activity and/or may be identified, used or analyzed.

In some embodiments, the in-vivo imaging device may illuminate at a certain (e.g., constant or variable) illumination pulse frequency, and/or may acquire images at a certain (e.g., constant or variable) frame capture rate. In one embodiment, the illumination pulse frequency and/or the frame capture rate may be relatively high, for example, relative to the velocity of contraction propagation in the body lumen. In another embodiment, the length of the contraction segment may be relatively large; this may allow, for example, acquisition of images which may be used for light intensity modulation analysis having a relatively higher accuracy. For example, in some embodiments, a relatively larger size of the contraction segment may more significantly affect the size or shape of the body lumen or a cavity therein, and may more significantly affect the light intensity modulation which may be used for contractile activity analysis or determination.

In some embodiments, frequency of contractions, or absence of contractile activity, may be determined from the modulation of the average image light intensity, and may be used as parameters for generating determinations with regard to motility, contractile activity, or medical conditions related to motility or contractile activity.

In some embodiments, frequency, amplitude, and/or period of contractile activity may be used for determining motility, or for creating a diagnosis having motility information. In one embodiment, such parameters of frequency, amplitude, and/or period of contractile activity may be derived from the light intensity modulation signal (e.g., of graph 1700), or from other suitable data, for example, velocity of the in-vivo device, changes in velocity of the in-vivo device, displacement of the in-vivo device, localization data, position data, acceleration data, or other data. In one embodiment, frequency, amplitude, and/or period of contractile activity may correlate to, or be in relation to, for example, velocity of the in-vivo device, changes in velocity of the in-vivo device, displacement of the in-vivo device, localization data, position data, acceleration data, or other data.

In some embodiments, one or more images acquired by the in-vivo device may be analyzed to allow determinations with regard to contractile activity. In one embodiment, for example, analysis of one or more images may indicate a sudden and/or short-term change in brightness level of one or more image, thereby allowing a possible determination that a relatively high contractile activity (e.g., one or more contractions) took place during the time period associated with the identified change in brightness level.

Although some portions of the discussion herein may relate, for exemplary purposes, to light intensity, illumination intensity, brightness level and/or darkness level, embodiments of the invention are not limited in this regard. Some embodiment may include determination of motility information, contractile activity information and/or contractions based on other data or parameters, for example, contrast, color, saturation, hue, one or more color channels, parameters or values which may be used before or after an enhancement process or a gain process is applied to such parameters or values, or the like.

Some embodiments of the invention may include, for example, an in-vivo imaging device having multiple imagers or image sensors, e.g., two or three imagers. For example, in one embodiment, the in-vivo device may include a first imager having a first field of view, and a second imager having a second field of view. In some embodiments, the multiple imagers may face different directions, e.g., at an angle of approximately 45 degrees, at an angle of approximately 90 degrees, at an angle of approximately 180 degrees, or the like. In some embodiments, the in-vivo device having multiple imagers may be used for collection of data which may be used for generating or analyzing motility data, contractions data, or contractile activity data. For example, multiple imagers of the in-vivo device may acquire images, which may be used for image comparison and/or light intensity modulation analysis, thereby allowing determinations with regard to motility, contractions, or contractile activity. In one embodiment, acquired data may be accumulated multiple imagers; in another embodiment, data acquired from each imager may be processed separately and the results may be compared or further analyzed; other suitable processes may be used.

Devices, systems and methods in accordance with some embodiments of the invention may be used, for example, in conjunction with a device which may be inserted into a human body or swallowed by a person. However, embodiments of the invention are not limited in this regard, and may be used, for example, in conjunction with a device which may be inserted into, or swallowed by, a non-human body or an animal body.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

What is claimed is:

1. A system comprising:
a processor to determine contractile activity within a body lumen based on an analysis of data received from an autonomous in-vivo device;
wherein said processor calculates a velocity of said in-vivo device within a pre-defined period of time, identifies a pattern in a plurality of calculated velocities, and determines said contractile activity based on said pattern of calculated velocities.

2. The system of claim 1, wherein said processor is to determine said contractile activity based on an analysis of localization data of said in-vivo device.

3. The system of claim 1, wherein said processor is to calculate a displacement of said in-vivo device within a pre-defined period of time and to determine said contractile activity based on said displacement.

4. The system of claim 3, wherein said processor is to determine a low contractile activity based on a small displacement of said in-vivo device within said pre-defined period of time.

5. The system of claim 1, wherein said processor is to determine said contractile activity based on a change of said velocity within said pre-defined period of time.

6. The system of claim 1, wherein said in-vivo device comprises a swallowable capsule.

7. The system of claim 1, wherein said processor is to determine said contractile activity based on an analysis of at least one image captured by said in-vivo device.

8. The system of claim 7, wherein said processor is to determine said contractile activity based on a brightness level of said at least one image.

9. The system of claim 1, wherein said processor is to determine said contractile activity based on modulation of light intensity of a plurality of images acquired by said in-vivo device.

10. A system comprising:
a processor to determine contractile activity within a body lumen based on an analysis of data received from an autonomous in-vivo device, wherein said processor identifies a pattern in localization data of said in-vivo device and determines said contractile activity based on said pattern.

11. A system comprising:
a processor to determine contractile activity within a body lumen based on an analysis of data received from an autonomous in-vivo device, wherein said processor calculates localization data of said in-vivo device based on a Radio Frequency signal received from said in-vivo device and determines said contractile activity based on an analysis of localization data of said in-vivo device.

12. A method comprising:
receiving data from an autonomous in-vivo device, said data including localization data;
identifying a pattern in said localization data; and
determining contractile activity within a body lumen based on an analysis of said pattern of localization data of said in-vivo device.

13. The method of claim 12, wherein determining comprises:
calculating a displacement of said in-vivo device within a pre-defined period of time; and
determining said contractile activity based on said displacement.

14. The method of claim 12, comprising determining said contractile activity based on an analysis of at least one image captured by said in-vivo device.

15. A method comprising:
receiving data from an autonomous in-vivo device;
calculating a velocity of said in-vivo device within a pre-defined period of time;
identifying a pattern in a plurality of calculated velocities; and
determining contractile activity within a body lumen based on said pattern of calculated velocities.

16. The method of claim 15, further comprising calculating a plurality of velocities of said in-vivo device.

* * * * *